(12) United States Patent
Monti

(10) Patent No.: US 12,171,891 B2
(45) Date of Patent: Dec. 24, 2024

(54) STERILISATION TUNNEL OF PHARMACEUTICAL CONTAINERS

(71) Applicant: MARCHESINI GROUP S.p.A., Pianoro (IT)

(72) Inventor: Giuseppe Monti, Pianoro (IT)

(73) Assignee: Marchesini Group S.P.A. (IT)

( * ) Notice: Subject to any disclaimer, the term of this patent is extended or adjusted under 35 U.S.C. 154(b) by 602 days.

(21) Appl. No.: 17/614,781

(22) PCT Filed: Jun. 9, 2020

(86) PCT No.: PCT/IB2020/055406
§ 371 (c)(1),
(2) Date: Nov. 29, 2021

(87) PCT Pub. No.: WO2020/250127
PCT Pub. Date: Dec. 17, 2020

(65) Prior Publication Data
US 2022/0226515 A1    Jul. 21, 2022

(30) Foreign Application Priority Data
Jun. 10, 2019   (IT) .................. 102019000008445

(51) Int. Cl.
*A61L 2/04* (2006.01)
*A61L 2/26* (2006.01)

(52) U.S. Cl.
CPC .................. *A61L 2/04* (2013.01); *A61L 2/26* (2013.01); *A61L 2202/122* (2013.01); *A61L 2202/23* (2013.01)

(58) Field of Classification Search
None
See application file for complete search history.

(56) References Cited

U.S. PATENT DOCUMENTS 5,022,165 A * 6/1991 Beswick ................. B65B 55/10
                                                                422/115
5,035,101 A    7/1991 Wakabayashi

FOREIGN PATENT DOCUMENTS

WO    WO-2017158118 A1 *  9/2017 ............... A61L 2/00

* cited by examiner

*Primary Examiner* — Jelitza M Perez
(74) *Attorney, Agent, or Firm* — Endurance Law Group PLC

(57) ABSTRACT

A sterilization tunnel has an inlet opening for pharmaceutical containers to be sterilised, an outlet opening, a high-temperature sterilisation chamber and a cooling chamber in line therewith and communicating with the outlet opening. A conveyor means transports the containers through the sterilisation chamber and the cooling chamber up to the outlet opening. A transfer plane is positionable in a first configuration aligned with the conveyor to transfer the containers out of the tunnel through the outlet opening. A shutter opens and closes the outlet opening. The transfer plane is movable and positionable in a second configuration inside the cooling chamber and misaligned with respect to the conveyor. When the transfer plane is inside the cooling chamber, the shutter is lowerable in abutment with a seal element.

7 Claims, 5 Drawing Sheets

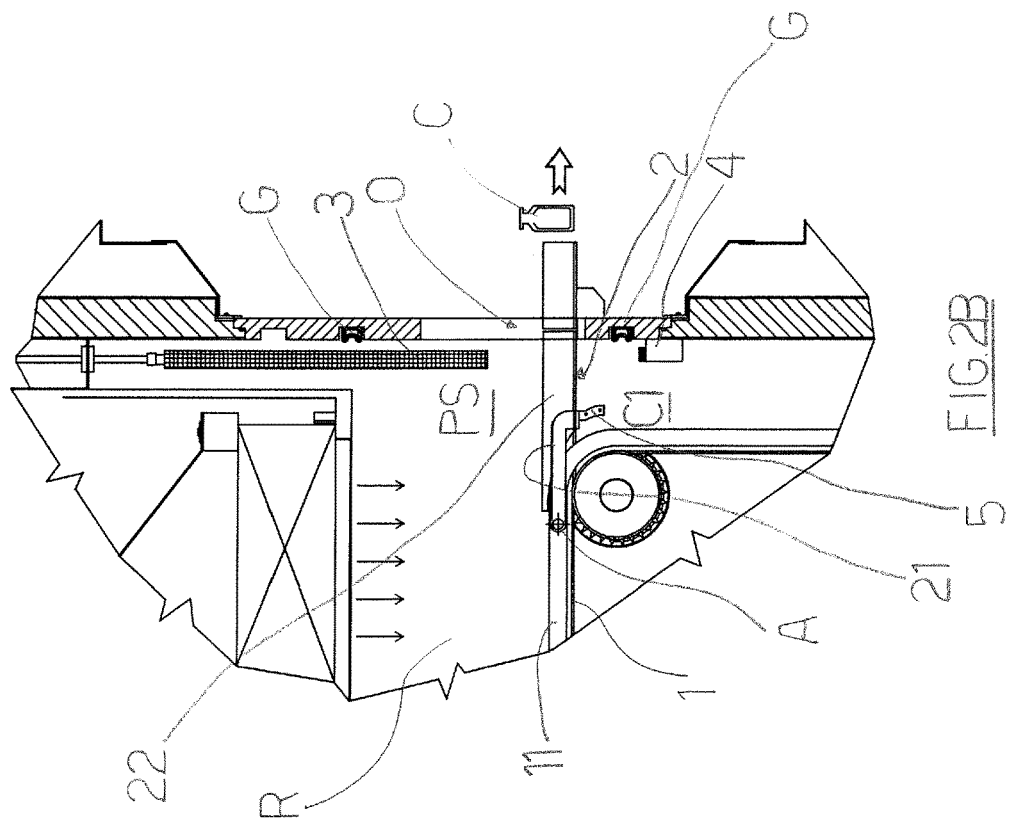
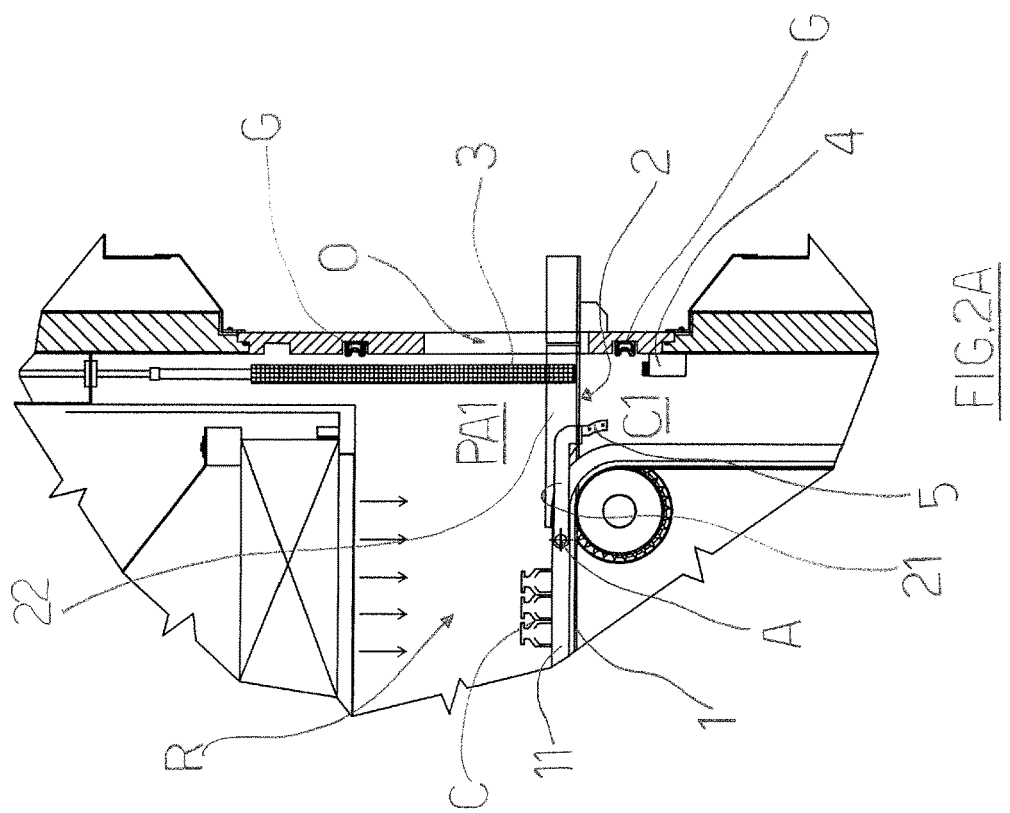

STERILISATION TUNNEL OF PHARMACEUTICAL CONTAINERS

FIELD OF THE INVENTION

The present invention relates to the technical sector concerning the filling of containers, such as for example bottles, vials and the like, with pharmaceutical products, such as for example tablets, capsules or compounds in liquid form, etc.

In particular, the present invention relates to a sterilisation tunnel of pharmaceutical containers through which the pharmaceutical containers, which are to be filled, are made to transit in order to be subjected to sterilisation.

DESCRIPTION OF THE PRIOR ART

It is known that before proceeding with the inserting of pharmaceutical products internally of relative containers, the containers must be subjected to appropriate sterilisation, with the purpose of eliminating the presence of any contaminating agents or residues.

In this regard, the containers to be sterilised are made to transit internally of a sterilisation tunnel that is usually positioned upstream of a filling machine, or upstream of an accumulating station, for example constituted by a turn table, in which the containers are accumulated prior to being directed internally of the filling machine.

A sterilisation tunnel of the prior art comprises a closed environment having an inlet opening for the containers and an outlet opening for the containers, and a conveyor means, predisposed to receive the containers through the inlet opening and transport them to the outlet opening.

Inside the tunnel, between the inlet opening and the outlet opening, there is at least a sterilisation chamber through which, via the conveyor means, the containers are made to transit.

For example, inside the tunnel there can be located, one following another: a pre-heating chamber, predisposed to carry out a pre-heating of the containers, a sterilisation chamber, internally of which high temperatures are reached, suitable for effectively carrying out the sterilisation of the containers, and a cooling chamber, internally of which the containers are struck by a flow of filtered air to lower the temperature thereof before being transported out of the tunnel via the outlet opening.

The conveyor means, for example a loop-closed belt or mat, extends up to almost in proximity of the outlet opening, having a winding end located in proximity of the outlet opening.

A transfer plane of the containers is positioned downstream, and consecutively, of the conveyor means, which transfer plane receives the sterilised containers from the conveyor means and enables passage thereof through the outlet opening outside the tunnel.

In this regard, a pusher member can be used to push the containers to slide on the transfer plane and through the outlet opening.

At the outlet opening, the tunnel is provided with a closing shutter which is movable between a raised position, to open the outlet opening and allow passage of the containers, and a lowered position, in which it is lowered and positioned abutting the transfer plane, to close the outlet opening.

Once the sterilisation cycle of a series of containers has completed, which are then to be filled with relative pharmaceutical products, and prior to proceeding with a subsequent sterilisation cycle of a second series of containers to be filled, it is necessary to proceed with the sterilisation of the cooling chamber, with the aim of eliminating the presence of any contaminating substances/agents that, in the meantime, might have been deposited internally of the cooling chamber, for example in the time during which the shutter has been kept in the raised position to allow the passage of the containers.

In this regard, the shutter is positioned in the lowered position, abutting the transfer plane, and the cooling chamber is struck by the flow of filtered hot air to reach high temperatures that are suitable for sterilisation.

However, the parts of the transfer plane covered by the shutter will not be struck by the hot air flows, and therefore as a consequence cannot have been adequately sterilised.

Another sterilisation tunnel of known type is described in document WO2017/158118.

This document describes a packaging plant comprising the combination of a sterilisation tunnel, of the above-described type, and a filling machine arranged consecutively to the sterilisation tunnel and having a conveyor for receiving the containers in outlet from the outlet opening of the tunnel, consecutive to the transfer plane of the sterilisation tunnel which is located at the shutter.

In this document, the transfer plane is movable between a first position, in which it is arranged at the outlet opening, between the conveyor means inside the sterilisation tunnel and the conveyor of the filling machine, and a second position, in which the transfer plane is brought into a position external of the sterilisation tunnel, beyond the outlet opening, and internal of the filling machine.

In this way, at the end of a production cycle, and before carrying out a following production cycle of sterilisation and filling of further containers, the transfer plane can be brought out of the tunnel, through the outlet opening and positioned in the filling machine.

The shutter can then be lowered to close the outlet opening of the tunnel and the cooling chamber can be subjected to the action of the filtered hot air flow for the sterilisation thereof.

At the same time, the sterilisation operations of the relative components must be carried out inside the filling machine and, consequently, also the transfer plane positioned therein can be sterilised.

This kind of movement mode of the transfer plane present in the sterilisation tunnel, located downstream of the conveyor means and at the outlet opening, can be useful only in the case that the sterilisation tunnel is used in exclusive combination with a filling machine.

In fact, this type of sterilisation tunnel, with the transfer plane movable externally of the tunnel, cannot be used in all those cases where the sterilisation tunnel has to be used in combination with storage accumulating stations of the containers to be sterilised, such as for example turntables or carousels, from which the containers are then transferred to a filling machine. By keeping the transfer plane aligned to the conveyor means, and displacing the shutter in the lowered position in abutment to the transfer plane, and by carrying out the sterilisation operations of the cooling chamber, the issue previously signalled would remain, i.e. the parts of the transfer plane covered by the shutter would not be subjected to any sterilisation.

Further, by moving the transfer plane externally of the tunnel, and then lowering the shutter to close the outlet opening to carry out the sterilisation operations of the cooling chamber, the transfer plane, by remaining outside, will not be able to be subjected to any sterilisation action and, consequently, once returned internally of the tunnel and aligned to the conveyor means, might be a cause of contamination.

SUMMARY OF THE INVENTION

The aim of the present invention is therefore to provide a new sterilisation tunnel of pharmaceutical containers able to obviate the drawbacks previously shown to be present in the prior art sterilisation tunnels.

In particular, the aim of the present invention is therefore to provide a new sterilisation tunnel of pharmaceutical containers which enables effectively carrying out the sterilisation operations of the cooling chamber and all relative components, in particular of the transfer plane located downstream of the conveyor means and at the outlet opening, and which can be equally used in combination with a filling machine and in all those cases in which the sterilised containers must be priorly accumulated in an accumulating station before being directed into a filling machine.

The above aims are attained with a sterilisation tunnel of pharmaceutical containers according to the claims.

BRIEF DESCRIPTION OF THE DRAWINGS

The characteristics of a preferred but not exclusive embodiment of the sterilisation tunnel of pharmaceutical containers of the present invention are described in the following with reference to the accompanying tables of drawings, in which:

FIGS. 2A to 2F illustrate, in larger scale, the detail denoted by letter K in FIG. 1, in which some significant components of the sterilisation tunnel are represent in various possible operating configurations;

DESCRIPTION OF THE PREFERRED EMBODIMENTS

With reference to the appended tables of drawings, reference letter (T) denotes the sterilisation tunnel of pharmaceutical containers of the present invention.

Figure 1:
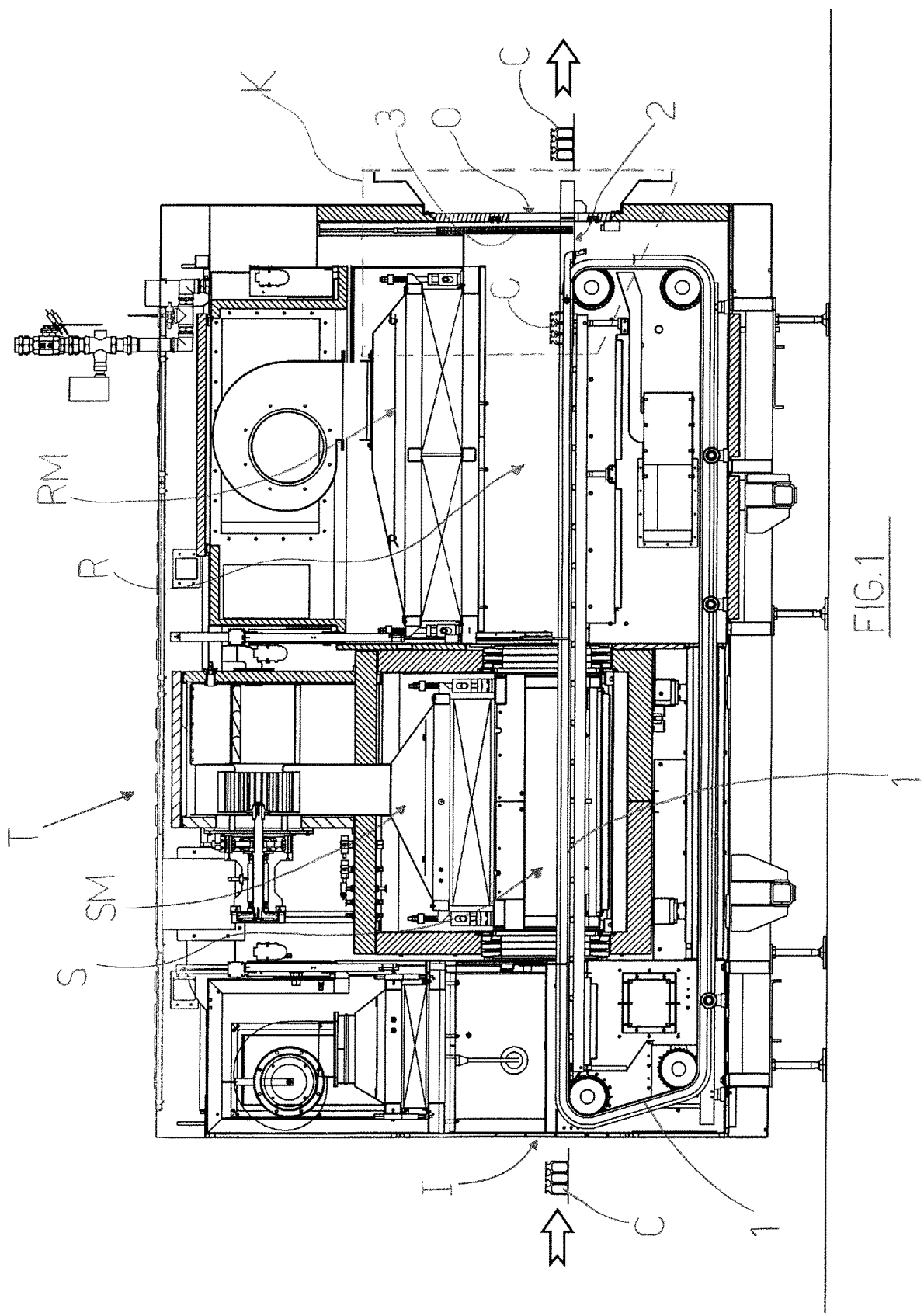
FIG. 1 is a lateral view in vertical section of the sterilisation tunnel of the invention.

The sterilisation tunnel (T) is realised in such a way as to comprise (see for example FIG. 1):

an inlet opening (I), for inlet of containers (C) to be sterilised, an outlet opening (O), for outlet of the sterilised containers (C);
at least a sterilisation chamber (S), for sterilisation of the containers at high temperature, and a cooling chamber (R), for cooling the sterilised containers, consecutive to the sterilisation chamber (S) and communicating with the outlet opening (O).
a conveyor means (1), for receiving the containers (C) from the inlet opening (I) and for transporting the containers (C) through the sterilisation chamber (S) and the cooling chamber (R) up to in proximity of the outlet opening (O).

Ventilation means (SM) (not described in detail as of known type and not an object of the present invention) are present in the sterilisation chamber (S), to direct flows of air filtered towards the containers transported by the conveyor means, and heating means (not illustrated), to heat the air flows so as to raise the temperature inside the sterilisation chamber (S) up to a sufficient amount to carry out the sterilisation of the containers.

Ventilation means (SM) are also present internally of the cooling chamber (R) (also not described in detail as of known type and not an object of the present invention), to direct flows of air (at ambient temperature or at a lower temperature) towards the containers transported by the conveyor means, and which have exited the sterilisation chamber, to lower the temperature thereof. The tunnel (T) further comprises a transfer plane (2), situated consecutive to the conveyor means (1) and mounted with respect to the conveyor means (1) so as to be arrangeable in a first alignment configuration (C1), wherein it is aligned to the conveyor means (1) and arranged at the outlet opening (O), in order to receive the sterilised containers (C) from the conveyor means (1) and enable transfer thereof externally of the tunnel (T) through the outlet opening (O).

The tunnel (T) further comprises a shutter (3), arranged and movable with respect to the outlet opening (O) and with respect to the transfer plane (2) so as to be positionable in a raised position (PS), in order to maintain the outlet opening (O) open and enable outlet of the sterilised containers (C), and in a first lowered position (PA1), abutting the transfer plane (2), in order to close the outlet opening (O).

For example, before the start of a sterilisation cycle, the shutter (3) is positioned in the first lowered position (PA1), abutting the transfer plane (2), in order to close the outlet opening (O), while awaiting the arrival of the containers transported by the conveyor means (1) (see for example FIG. 1 and FIG. 2A), then to be raised into the raised position (PS) (see FIG. 2B), on the arrival of the sterilised and cooled containers, in order to open the outlet opening (O) and enable the passage of the containers, which have been transferred by the conveyor means above the transfer plane (2) externally of the tunnel.

To transfer the containers along the transfer plane, through the outlet opening, suitable pusher means can for example be used (not illustrated as of known type and not forming part of the object of the present invention).

Figure 2D:
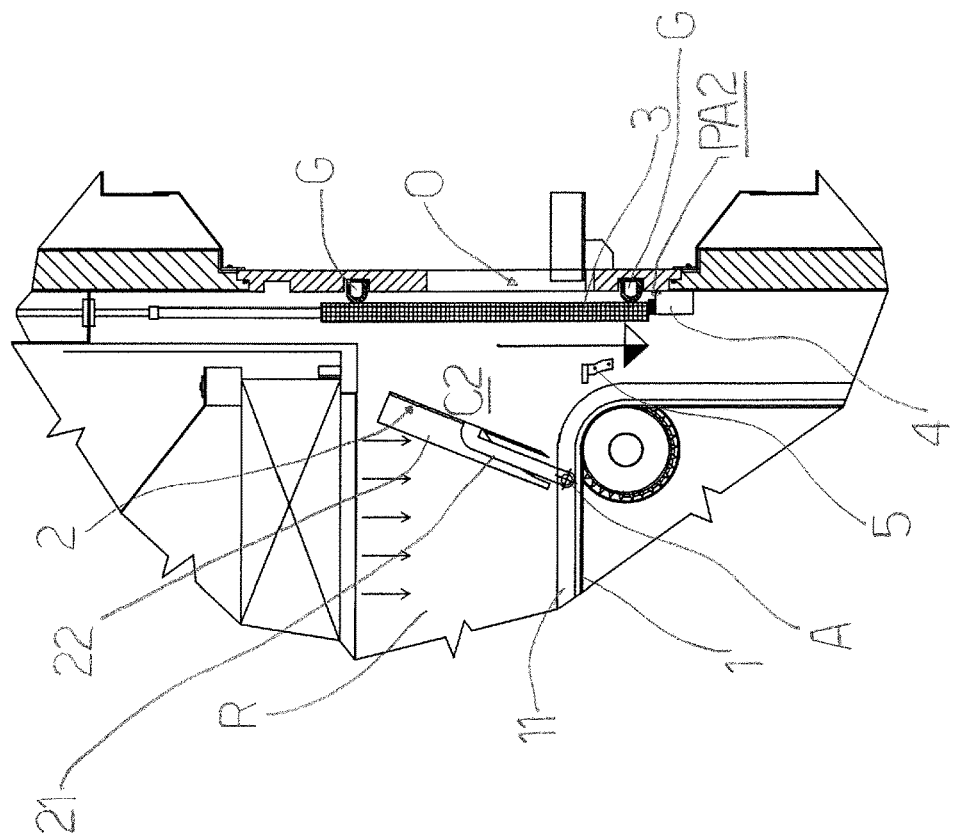
Figure 2C:
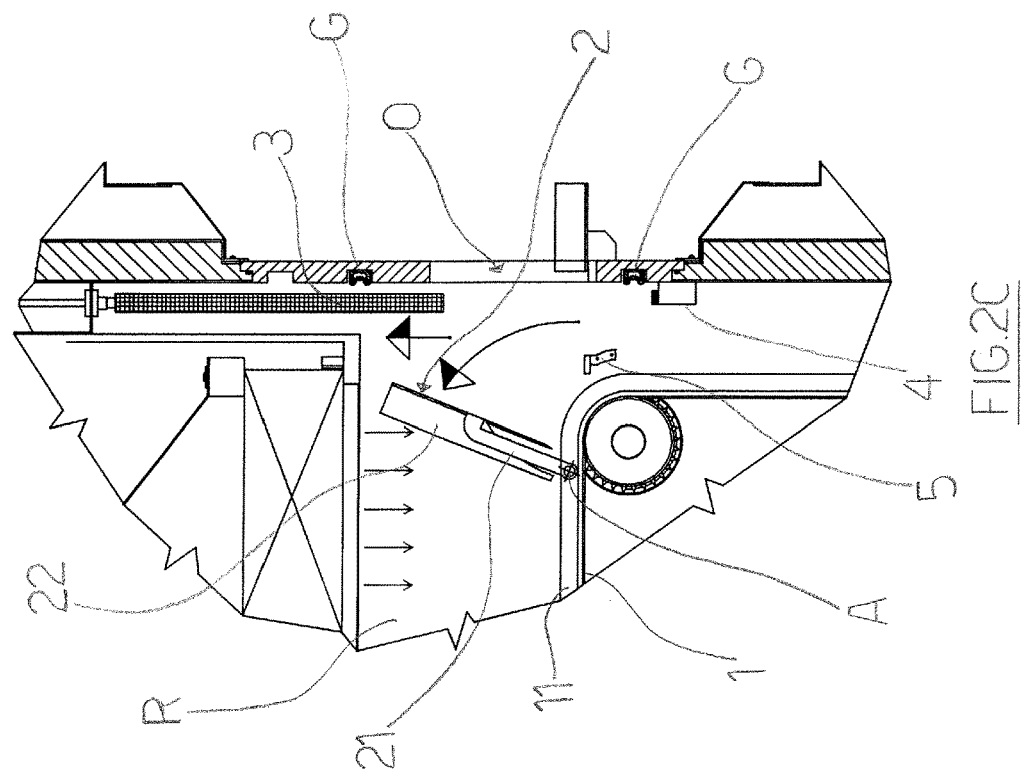

The special characteristics of the sterilisation tunnel (T) of the present invention consists of the fact that it is configured and realised in such a way that the transfer plane (2) is mounted with respect to the conveyor means (1) in such a way as to be movable and positionable in a second misaligned configuration (C2) with respect to the conveyor means (1) in which the transfer plane (2) is misaligned with respect to the conveyor means (1) and arranged internally of the cooling chamber (R) of the tunnel (T) (see in particular FIGS. 2C and 2D).

Further, another special aspect consists in the fact that the shutter (3), when the transfer plane (2) is moved and positioned in the second misaligned configuration (C2) and arranged internally of the cooling chamber (R), is movable in order to be positioned in a second lowered position (PA2) (FIG. 2D), at a lower height than the first lowered position (PA1), in which the shutter (3) is positioned abutting a seal element (4), in order to achieve the sealed closure of the cooling chamber (R) with respect to the outside environment.

In this way, owing to these particular characteristics, the transfer plane (2) can be borne inside the cooling chamber (R), and the cooling chamber (R) can be sealedly isolated from the external environment.

Consequently, between on sterilisation cycle of containers and the next, it is possible to effectively carry out the sterilisation operations of both the cooling chamber and all the transfer plane.

In this regard, in the cooling chamber (R) there are appropriate heating means (not illustrated), such as electrical resistances, for heating the filtered air flow directed towards the conveyor means (1) by the ventilation means (RM).

In particular, the transfer plane (2) is mounted with respect to the conveyor means (1) in such a way as to be movable with respect to the conveyor means (1) in order to be positionable in the second misaligned configuration (C2) so that the transfer plane (2) is arranged above the terminal part of the transfer plane (1) and below the heated air flows directed by the ventilation means (RM) towards the conveyor means (1), with a configuration that is inclined with respect to the vertical, so that the whole surface of the transfer plane can be struck by the heated air flows coming from the ventilation means (RM) (see in particular FIG. 2D).

Therefore, at the end of the sterilisation process of the cooling chamber (R), the whole of the transfer plane (2) will also have been perfectly sterilised. Then the shutter (3) can be raised and the transfer plane (2) returned into the first aligned configuration (C1) with the conveyor means (1), and the shutter (3) lowered into the first lowered position (PA1) against the transfer plane (2), to await the start of a following sterilisation cycle of another group of containers.

Owing to the peculiarities described in the foregoing, the sterilisation tunnel (T) of the present invention can be used equally in combination with both the filling machines and with the accumulation stations of the containers, as it is able to guarantee optimal sterilisation of the transfer plane, as it can be brought internally of the cooling chamber of the tunnel in order to be subjected to suitable and complete sterilisation during the sterilisation process of the cooling chamber.

Further and other characteristics of the sterilisation tunnel of the invention are described in the following.

It comprises lateral borders (11) for guiding the containers arranged at sides of the conveyor means (1) and wherein the transfer plane (2) is hinged to the lateral borders (11) at hinge points (A) and movable in rotation about the hinge points (A) with respect to the lateral borders (11) so as to be movable from the first aligned configuration (C1) with the conveyor means (1) into the second misaligned configuration (C2) from the conveyor means (1) to inside the cooling chamber (R) of the tunnel (T), and vice versa from the second configuration (C2) to the first configuration (C1).

In particular, according to the preferred but not exclusive embodiment illustrated in the figures, the transfer plane (2) is hinged to the lateral borders (11) by means of support arms (21), fixed on one side, bilaterally to the transfer plane (2) and, on the other side, hinged to the lateral borders (11) at the hinge points (A).

To rotate the transfer plane (2) about the hinge points (A), it is possible to use appropriate actuator means, such as for example at least a shaft mounted with the axis thereof at hinge points and constrained to the support arms (21), and activatable in rotation by a relative motor, or other equivalent activating systems.

Figure 4:
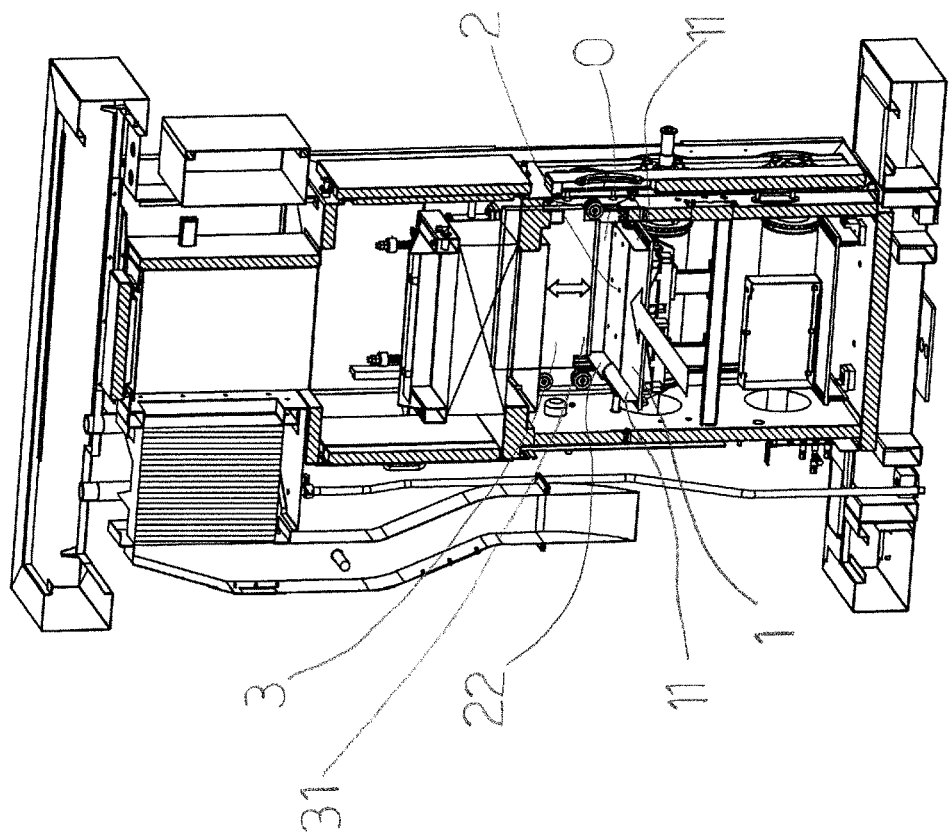
FIG. 4 is a partial schematic view in vertical section from inside of the part of the sterilisation tunnel in which the outlet opening of the containers is situated.
Figure 3:
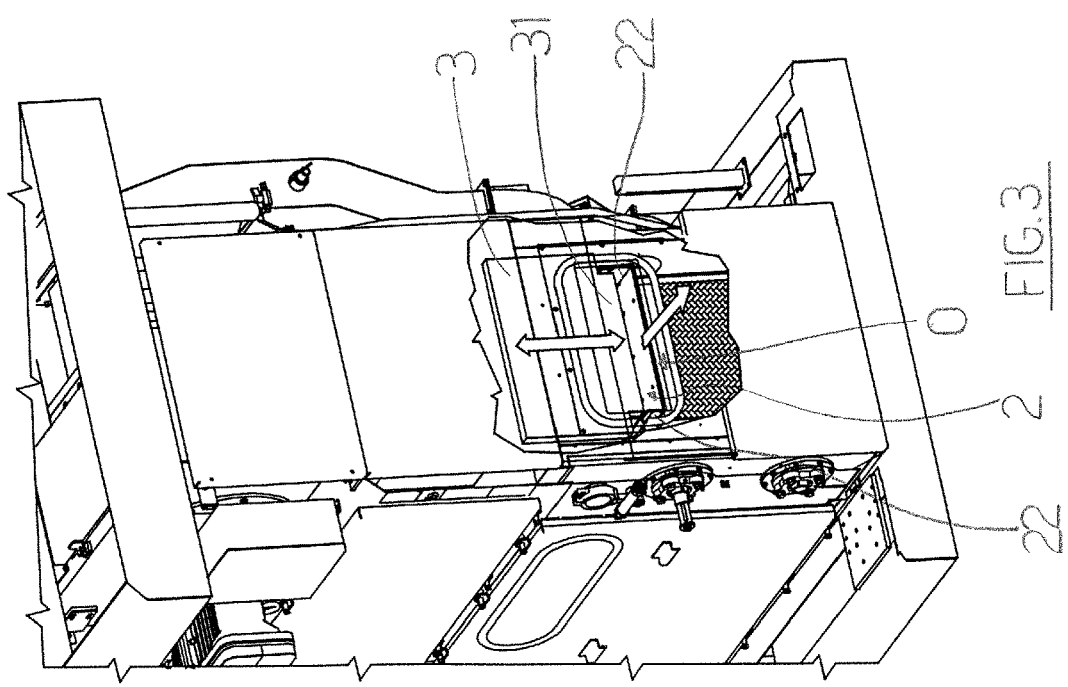
FIG. 3 is a partial schematic front view from outside of the part of the sterilisation tunnel in which the outlet opening of the containers is situated.

The transfer plane (2) can comprise lateral walls (22), for containing and guiding the containers (C) during the passage thereof through the outlet opening (O), while the shutter (3) comprises a lower portion (30) conformed in such a way as to have a projecting central part (31) having dimensions such as to be able to insert between the lateral walls (22) and abut the transfer plane (2), when the shutter (3) is positioned in the first lowered position (PA1) (see for example FIGS. 3 and 4).

Figure 2F:
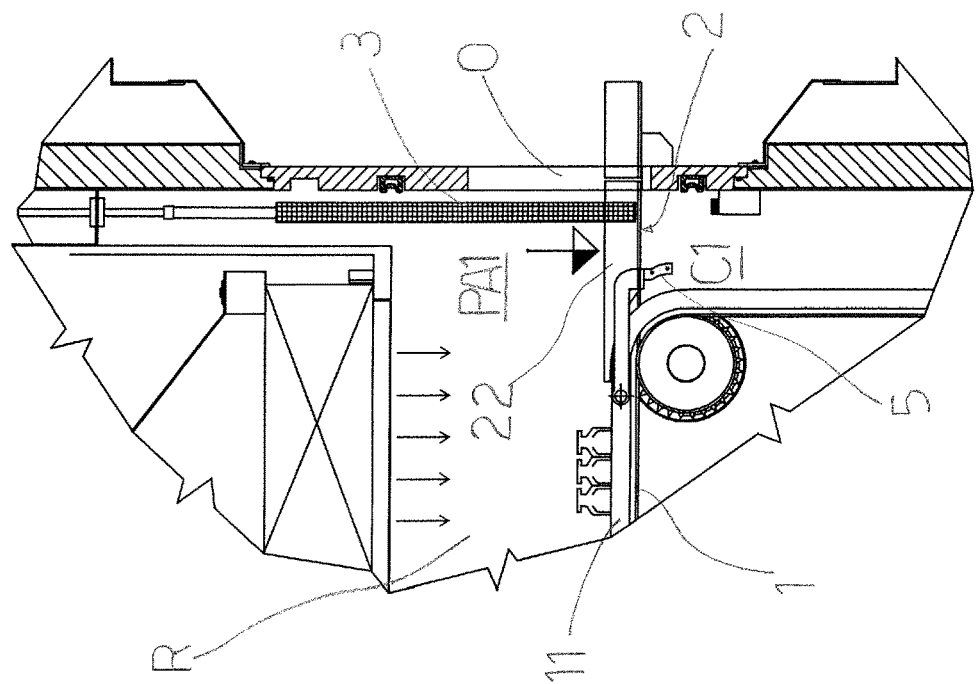
Figure 2E:
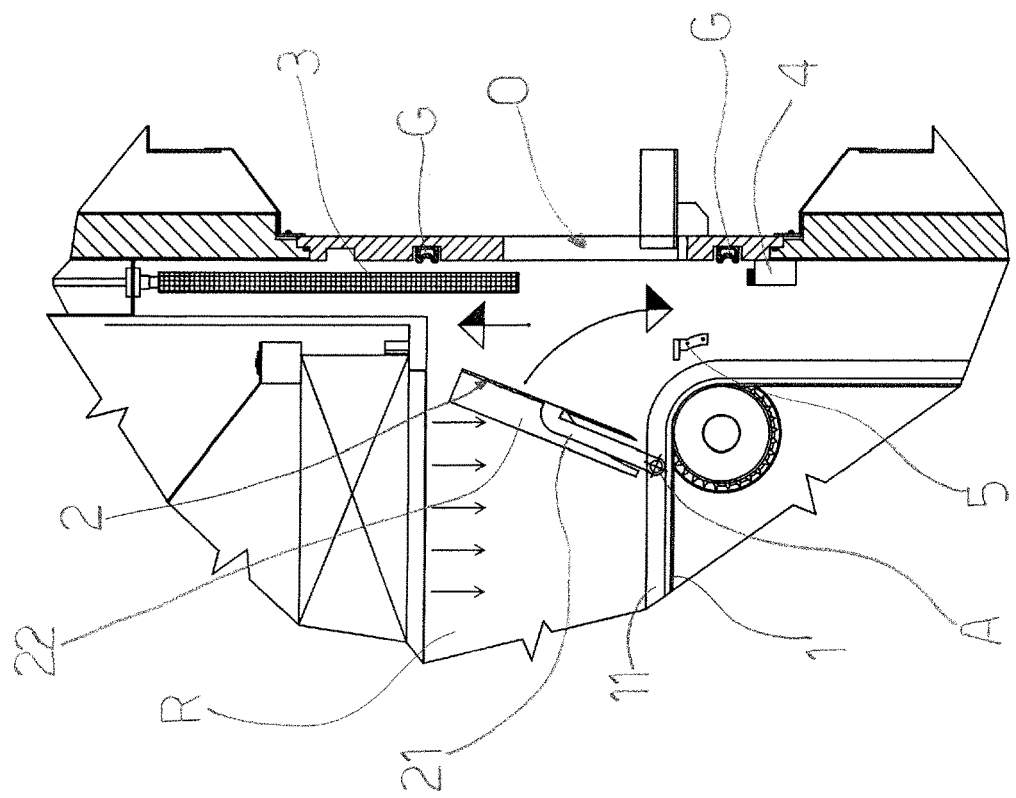

A further particular aspect relates to the fact that the shutter (3), when the transfer plane (2) is to be moved and positioned from the first aligned configuration (C1) to the second misaligned configuration (C2), and vice versa from the second misaligned configuration (C2) to the first aligned configuration (C1), is raisable to a height that is such as to free a manoeuvring space sufficient to move and displace the transfer plane (2) (see FIGS. 2C and 2E). The sterilisation tunnel (T) can advantageously comprise an abutment element (5) which is positioned between the conveyor means (1) and the outlet opening (O) in a position such as to constitute an abutment and a support for the transfer plane (2) when the transfer plane (2) is positioned in the first aligned configuration (C1) to the conveyor means (1), in order to maintain the transfer plane (2) aligned to the conveyor means (1) of the outlet opening (O) (see for example FIGS. 2A, 2B and 2F).

The tunnel (T) further comprises an inflatable seal (G) arranged peripherally about the outlet opening (O), internally of the tunnel (T).

The inflatable seal (G) is maintained uninflated and therefore retracted, when the shutter (3) has to be moved with respect to the outlet opening (O), between the raised position (PS) and the first lowered position (PA1) (see for example FIGS. 2A, 2B, 2C, 2E and 2F), and is inflated and thus expanded, in order to abut the shutter (3) when the shutter (3) is positioned in the second lowered position (PA2) to abut the seal element (4) (see FIG. 2D), and guarantee the sealed closure of the cooling chamber (R) with respect to the outside environment.

From the above description, the sterilisation tunnel of the present invention effectively obviates the drawbacks present in the sterilisation tunnel of the prior art, relative to the sterilisation of the transfer plane, enabling the sterilisation tunnel of the invention to be utilisable both in combination directly with a filling machine and with accumulation stations of the containers.

The invention claimed is:

1. A sterilisation tunnel of pharmaceutical containers, comprising:
   an inlet opening, for inlet of containers to be sterilised,
   an outlet opening, for outlet of the sterilised containers;
   at least a sterilisation chamber, for sterilisation of the containers at high temperature, and a cooling chamber, for cooling the sterilised containers, consecutive to the sterilisation chamber and communicating with the outlet opening;
   a conveyor means, for receiving the containers from the inlet opening and for transporting the containers through the sterilisation chamber and the cooling chamber up to in proximity of the outlet opening;
   a transfer plane, situated consecutive to the conveyor means, wherein the transfer plane is mounted with respect to the conveyor means so as to be arrangeable in a first alignment configuration, wherein it is aligned to the conveyor means and arranged at the outlet opening, in order to receive the sterilised containers from the conveyor means and enable transfer thereof externally of the tunnel through the outlet opening;
   a shutter, arranged and movable with respect to the outlet opening and with respect to the transfer plane so as to be positionable in a raised position, in order to maintain the outlet opening open and enable outlet of the sterilised containers, and in a first lowered position, abutting the transfer plane, in order to close the outlet opening;

wherein the transfer plane is mounted with respect to the conveyor means in such a way as to be movable and positionable in a second misaligned configuration with respect to the conveyor means wherein the transfer plane is misaligned with respect to the conveyor means and arranged internally of the cooling chamber of the tunnel, and in that the shutter, when the transfer plane is moved and positioned in the second misaligned configuration and arranged internally of the cooling chamber, is movable in order to be positioned in a second lowered position, at a lower height than the first lowered position, in which the shutter is positioned abutting a seal element.

2. The sterilisation tunnel of claim 1, further comprising lateral borders for guiding the containers arranged at sides of the conveyor means and wherein the transfer plane is hinged to the lateral borders at hinge points and movable in rotation about the hinge points with respect to the lateral borders so as to be movable from the first alignment configuration with the conveyor means into the second misaligned configuration from the conveyor means to inside the cooling chamber of the tunnel, and vice versa from the second configuration to the first configuration.

3. The sterilisation tunnel of claim 2, wherein the transfer plane is hinged to the lateral borders by means of support arms, fixed on one side, bilaterally to the transfer plane and, on the other side, hinged to the lateral borders at the hinge points.

4. The sterilisation tunnel of claim 3, wherein the transfer plane comprises lateral walls, for containing and guiding the containers during the passage thereof through the outlet opening, and wherein the shutter comprises a lower portion conformed in such a way as to have a projecting central part having dimensions such as to be able to insert between the lateral walls and abut the transfer plane, when the shutter is positioned in the first lowered position.

5. The sterilisation tunnel of claim 1, wherein the shutter, when the transfer plane is to be moved and positioned from the first aligned configuration to the second misaligned configuration, and vice versa from the second misaligned configuration to the first aligned configuration, is raisable to a height that is such as to free a maneuvering space sufficient to move and displace the transfer plane.

6. The sterilisation tunnel of claim 1, further comprising an abutment element positioned between the conveyor means and the outlet opening in a position that is such as to constitute an abutment and a support for the transfer plane when the transfer plane is positioned in the first aligned configuration to the conveyor means, in order to maintain the transfer plane aligned to the conveyor means of the outlet opening.

7. The sterilisation tunnel of claim 1, further comprising an inflatable seal arranged peripherally about the outlet opening, internally of the tunnel, the inflatable seal being maintained uninflated and therefore retracted, when the shutter has to be movable with respect to the outlet opening, between the raised position and the first lowered position, and being inflatable and thus expandable in order to abut the shutter when the shutter is positioned in the second lowered position to abut the seal element.

* * * * *